United States Patent
Detering et al.

(10) Patent No.: US 6,916,778 B1
(45) Date of Patent: Jul. 12, 2005

(54) UV ABSORBERS WITH AFFINITY FOR TEXTILE FIBER

(75) Inventors: Jürgen Detering, Limburgerhof (DE); Werner Bertleff, Viernheim (DE); Gerhard Wagenblast, Wachenheim (DE); Christian Ott, Speyer (DE); Elisabeth Kappes, Limburgerhof (DE); Thorsten Habeck, Meckenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/926,412

(22) PCT Filed: Apr. 17, 2000

(86) PCT No.: PCT/EP00/03464

§ 371 (c)(1),
(2), (4) Date: Oct. 29, 2001

(87) PCT Pub. No.: WO00/65142

PCT Pub. Date: Nov. 2, 2000

(30) Foreign Application Priority Data

Apr. 27, 1999 (DE) .......................................... 199 18 967
Dec. 6, 1999 (DE) .......................................... 199 58 703

(51) Int. Cl.$^7$ ................................................ C11D 3/32
(52) U.S. Cl. ..................... 510/501; 252/8.61; 252/8.81; 252/8.91; 252/397; 564/170; 564/153
(58) Field of Search ................................ 252/397, 8.61, 252/8.81, 8.91; 510/501, 502; 564/170, 153

(56) References Cited

U.S. PATENT DOCUMENTS

| | | |
|---|---|---|
| 3,030,208 A | 4/1962 | Schellenberg et al. |
| 3,272,855 A | 9/1966 | Strobel et al. |
| 4,366,207 A | 12/1982 | Anthony |
| 4,701,497 A | 10/1987 | Serizawa et al. |
| 4,726,942 A | 2/1988 | Lang et al. |
| 5,474,691 A | 12/1995 | Severns |
| 5,601,811 A | 2/1997 | Gallagher et al. |
| 5,830,441 A | 11/1998 | Wang et al. |
| 5,888,481 A | 3/1999 | Horn et al. |
| 6,090,374 A | 7/2000 | Habeck et al. |

FOREIGN PATENT DOCUMENTS

| | | |
|---|---|---|
| DE | 1 119 510 | 12/1961 |
| DE | 196 53 892 | 6/1998 |
| DE | 197 55 650 | 4/1999 |
| EP | 0 523 955 | 1/1993 |
| EP | 0 682 145 | 11/1995 |
| EP | 0 728 749 | 8/1996 |
| GB | 1 246 236 | 9/1971 |
| GB | 2 313 375 | 11/1997 |

*Primary Examiner*—Shailendra Kumar
(74) *Attorney, Agent, or Firm*—Oblon, Spivak, McClelland, Maier & Neustadt, P.C.

(57) ABSTRACT

The invention relates to the use of compounds (A) with at least one structural unit of formula (I), wherein X represents groups of formula —$CR^1$=$CR^2$— or a carbonyl group C=O, $R^1$ and $R^2$ meaning hydrogen or essentially organic radicals, Z means essentially organic radicals, n means a number from 0 to 3 and p means a number from 0 to 5, as UV absorbers with an affinity for textile fibres, for protecting the human skin from harmful UV radiation and for protecting dyed textile materials from fading.

8 Claims, No Drawings

UV ABSORBERS WITH AFFINITY FOR TEXTILE FIBER

This application is a 371 of PCT/EP00/03464, filed Apr. 17, 2000.

BACKGROUND OF THE INVENTION

1. Field of the Invention

The present invention relates to the use as UV absorbers with affinity for textile fiber of compounds containing a certain structural unit responsible for UV absorption, and also a method for protecting human skin against harmful UV radiation and a method for protecting dyed textile material against fading, and also a method for increasing the UV protection factor UPF for textile material, also a laundry detergent and a laundry pre- and aftertreatment which include these UV absorbers with affinity for textile fiber and also—since some of these UV absorbers with affinity for textile fiber are novel—these novel substances themselves and also a process for preparing them and a textile material comprising these UV absorbers with affinity for fiber.

2. Description of the Background

The harmful effects on human skin of the UV content of sunlight are not restricted to premature skin aging and the formation of erythemas (skin reddening, sunburn). Excessively long and intensive exposure of the skin to UV radiation also raises the risk of developing skin cancer. The chief culprit responsible for skin reddening and the increased risk of skin cancer is the UV-B range of UV radiation, i.e., the range from 280 to 320 nm. The peak of the erythema action spectrum is located at 308 nm.

Textiles absorb UV radiation and so act as a physical barrier to protect the skin against the harmful effects of sunlight ("textile skin protection"). However, the skin-protecting effect of textiles is dependent on many factors such as fiber type, fabric construction, fabric weight, color, moisture content or nature of finish. Summer clothing in the form of lightweight and light-colored cotton textiles offers only slight and hence inadequate protection against UV radiation.

It is mainly customary optical brighteners which have hitherto been used to finish and protect the textiles themselves and also for textile skin protection, especially stilbene- and triazine-based optical brighteners as described for example in EP-A 682 145, GB-A 2 313 375 or EP-A 728 749. But the agents are still in need of improvement with regard to their efficacy and possess a number of disadvantages.

It is an object of the present invention to provide UV absorbers which have affinity for fiber, which are improved in their efficacy and which are free of the disadvantages of the prior art.

SUMMARY OF THE INVENTION

We have found that this object is achieved by the use of compounds (A) containing at least one structural unit, frequently preferably at least two structural units, of the general formula (I)

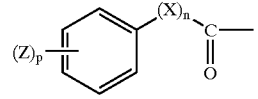

where

X is a group of the formula $-CR^1=CR^2-$ or a carbonyl group $C=O$, where $R^1$ and $R^2$ are independently hydrogen, $C_1$- to $C_8$-alkyl, $C_1$- to $C_8$-alkoxy, $C_1$- to $C_8$-alkoxycarbonyl, $C_1$- to $C_8$-acyloxy, carboxyl, cyano, nitro, fluorine, chlorine, bromine, sulfonyl, $C_1$- to $C_8$-alkylsulfonyl or phenyl which may be substituted by up to 3 radicals selected from the group consisting of $C_1$- to $C_8$-alkyl, $C_1$- to $C_8$-alkoxy, $C_1$- to $C_8$-alkoxycarbonyl, $C_1$- to $C_8$-acyloxy, carboxyl, cyano, nitro, chlorine, bromine, sulfonyl and $C_1$- to $C_8$-alkylsulfonyl, Z is a substituent selected from the group consisting of $C_1$- to $C_8$-alkyl, $C_1$- to $C_8$-Alkoxy, $C_1$- to $C_8$-alkoxycarbonyl, $C_1$- to $C_8$-acyloxy, carboxyl, cyano, nitro, fluorine, chlorine, bromine, sulfonyl, $C_1$- to $C_8$-alkylsulfonyl, amino, mono- or di-$C_1$- to $C_8$-alkylamino, carboxamido (with or without one or two $C_1$- to $C_8$-alkyl groups on the amide nitrogen), hydroxyl and saturated or unsaturated five- and six-membered heterocyclic radicals, which may be benzofused, and any two adjacent Z substituents may also form a saturated or unsaturated five- or six-membered ring, and in the case of p=0 an ortho-disposed carboxyl group may be combined with the carbonyl group present and a nitrogen atom attached directly to this carbonyl group to form a cyclic imide, n is 0, 1, 2 or 3, preferably 0 or 1, and p is 0, 1, 2, 3, 4 or 5, preferably 0, 1, 2 or 3, as UV absorbers possessing affinity for textile fiber.

DETAILED DESCRIPTION OF THE PREFERRED EMBODIMENTS

The compounds (A) with at least one structural unit (I) are preferably useful—within the meaning of the stated object of the present invention—on textile material, for protecting human skin against harmful UV radiation. But they also protect the textile material itself against UV radiation and more particularly they protect dyed textile material against fading.

A preferred embodiment utilizes compounds (A) conforming to the general formula (II)

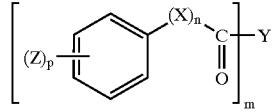

where

Y is the radical of an aliphatic, cycloaliphatic, aromatic or mixed aliphatic-aromatic group which has an average molar mass ($M_W$) of up to 100,000,000, which contains at least m' primary and/or secondary amino groups or m' hydroxyl groups or together at least m' primary and/or secondary amino groups and hydroxyl groups capable of forming amide or ester bonds with the structural unit (I) and which may also be quaternized at tertiary and/or free primary and/or secondary nitrogen atoms present or still present in the compounds (II), m' is from 1 to 200, subject to the provisos that the number m of the structural units (I) accounts for from 10 to 100% of m' and that, however, at least one structural unit (I) is present in the compounds (II),
and X, Z, n and p are each as defined above.

The number m of the structural units (I) in the compounds (II) varies with the size and structure of the Y group and is in particular within the range from 1 to 50, preferably from 1 to 10, particularly from 1 to 5, or from 2 to 50-, preferably from 2 to 10, particularly from 2 to 5. In most cases, m is 1, 2 or 3. The number m' of the amino or hydroxyl groups in the parent group of Y which are capable of linking to the structural units (I) can be a multiple of m; more particularly, m' is a number from 1 to 100, particularly from 1 to 50, or from 2 to 200, preferably from 2 to 100, particularly from 2 to 50. Preferably, m is from 20 to 100% of m' and particularly from 30 to 100% of m'.

The parent compounds of Y are in particular monomeric and polymeric aminoalcohols, oligo- and polyamines, polyalkylenepolyamines, polyamidoamines, polyvinylamines and (poly)ethyleneimine-grafted polyalkylenepolyamines, wherein the amines and aminoalcohols mentioned may also be quaternized at tertiary and/or free primary and/or secondary nitrogen atoms present or still present in the compounds (II). In the quaternized form, such nitrogen atoms generally bear as the fourth organic moiety a $C_1$- to $C_4$-alkyl group, usually a methyl or ethyl group, or a benzyl group, each of which has been introduced using customary methods.

In a particularly preferred embodiment, Y is the radical of an aliphatic or cycloaliphatic oligoamine which contains from 2 to 6 nitrogen atoms and a total of from 2 to 30 carbon atoms, which may additionally bear from 1 to 3 hydroxyl groups and which may also be quaternized at tertiary and/or free primary and/or secondary nitrogen atoms present or still present in the compounds (II). Typical examples of such oligoamines are 1,2-diaminoethane, 1,3-diaminopropane, 1,4-diaminobutane, diethylenetriamine, dipropylenetriamine, triethylentetramine, tetraethylenepentamine, pentaethylenehexamine, N-(2-aminoethyl)-1,3-propanediamine, N,N-dimethylethanolamine, diethanolamine, triethanolamine, 3-dimethylamino-1-propanol, N-(2-aminoethyl) ethanolamine, 3-(dimethylamino)propylamine, N,N'-bis(3-aminopropyl)-1,2-ethylenediamine, N,N,N',N'-tetrakis(3-aminopropyl)-1,2-ethylenediamine, N,N,N',N'-tetrakis[3-($C_1$- to $C_4$-alkylamino)propyl]-1,2-ethylenediamine, N,N'-bis(3-aminopropyl)piperazine and N,N'-bis[3-($C_1$- to $C_4$-alkylamino)propyl]piperazine. Suitable $C_1$- to $C_4$-alkyl radicals in the above-recited oligoamines are in each case methyl, ethyl, n-propyl, isopropyl, n-butyl, isobutyl, sec-butyl and tert-butyl.

In a further particularly preferred embodiment, Y is the radical of a polyethyleneimine of the general formula (III)

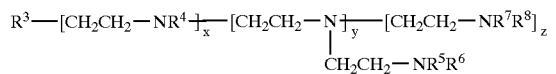

(III)

which has an average molar mass ($M_W$) of from 200 to 1,000,000 and in which $R^3$ to $R^8$ are independently hydrogen, linear or branched $C_1$- to $C_{20}$-alkyl, -alkoxy, -polyoxyethylene, -hydroxyalkyl, -(alkyl)carboxy, -phosphonoalkyl, -alkylamino radicals, $C_2$- to $C_{20}$-alkenyl radicals or $C_6$- to $C_{20}$-aryl, -aryloxy, -hydroxyaryl, -arylcarboxy or -arylamino radicals which may be further substituted, and $R^4$ and $R^5$ are each additionally further polyethyleneimine polymer chains, and x, y and z are independently 0 or an integer, and the polyethyleneimine mentioned may also be quaternized at tertiary and/or free primary and/or secondary nitrogen atoms present or still present in the compounds (II).

The sum of x, y and z must be chosen in such a way that the average molar mass is within the specified range. Preferred ranges for the average molar mass ($M_W$) of the polyethyleneimines (III) extend from 250 to 100,000, and particularly from 300 to 25,000.

$R^3$ to $R^8$ are each preferably hydrogen, methyl, ethyl, carboxymethyl, carboxyethyl, phosphonomethyl, 2-hydroxyethyl, 2-(2'-hydroxyethoxy)ethyl and 2-[2'-(2''-hydroxyethoxy)-ethoxy]ethyl.

In a further particularly preferred embodiment, Y is the radical of a polyamidoamine which has an average molar mass ($M_W$) of from 500 to 100,000,000, which is obtainable by reaction of $C_4$- to $C_{10}$-dicarboxylic acids with poly($C_2$- to $C_4$-alkylene)polyamines having from 3 to 20 basic nitrogen atoms in the molecule and which has at least m' primary and/or secondary amino groups capable of forming amide or ester bonds with the structural unit (I) and wherein the polyamidoamine mentioned may also be quaternized at tertiary and/or free primary and/or secondary nitrogen atoms present or still present in the compounds (II).

Preferred ranges for the average molar mass ($M_W$) of the polyamidoamines extend from 800 to 1,000,000 and particularly from 1200 to 200,000.

In a further particularly preferred embodiment, Y is the radical of a polyamine of the general formula (IV)

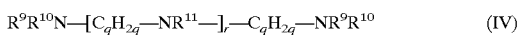

(IV)

which has an average molar mass ($M_W$) of from 100 to 100,000,000 and wherein $R^9$ to $R^{11}$ are independently hydrogen, linear or branched $C_1$- to $C_{20}$-alkyl, -alkoxy, -polyoxyethylene, -hydroxyaryl, -arylcarboxy or -arylamino radicals which may be further substituted, and $R^{15}$ is additionally a formamidyl, pyrrolidonyl or imidazolyl radical, s is an integer and t is 0 or an integer, wherein the polyvinylamine mentioned may also be quaternized at tertiary and/or free primary and/or secondary nitrogen atoms present or still present in the compounds (II).

The sum of s and t must be chosen in such a way that the average molar mass is within the specified range. Preferred ranges for the average molar mass ($M_W$) of the polyvinylamines (V) extend from 500 to 500,000, and in particular from 800 to 50,000.

Preferred meanings for $R^{12}$ to $R^{16}$ are again those specified above for $R^3$ to $R^8$.

Preference is further given to compounds (A) which contain one or more structural units (I) in which X is a group of the formula —$CR^1$=$CR^2$— where $R^1$ and $R^2$ are independently hydrogen, cyano or unsubstituted phenyl and n is 1.

Preference is further given to using compounds (A) which contain one or more structural units (I) in which Z is a substituent id selected from the group consisting of $C_1$- to $C_8$-alkoxy, amino, mono- or di-$C_1$- to $C_9$-alkylamino and hydroxyl and p is 1.

In connection with the abovementioned variables $R^1$, $R^2$ and Z, $C_1$- to $C_8$-alkyl, -alkoxy and -acyloxy are in particular methyl, ethyl, n-propyl, isoproypl, n-butyl, isobutyl, sec-butyl, tert-butyl, n-pentyl, n-hexyl, n-heptyl, n-octyl and 2-ethylhexyl and respectively the corresponding alkoxy or acyloxy radicals.

Examples of suitable saturated or unsaturated five- and six-membered heterocyclic radicals for the variable Z, which may be benzofused, are imidazolyl and benzimidazolyl.

An example of a suitable unsaturated six-membered ring which may be formed by two adjacent substituents Z is a benzofused ring.

Individual particularly preferred structural units (I) for the compounds (A) are:

p-Aminobenzoyl p-(Mono-$C_1$- to CB-alkylamino)benzoyl p-($D_1$—$C_1$- to $C_8$-alkylamino)benzoyl p-Hydroxycinnamoyl (derived from p-hydroxycinnamic acid)

p-$C_1$- to $C_8$-Alkoxycinnamoyl (derived from p-$C_1$- to $C_8$-alkoxycinnamic acid)

-hydroxyalkyl, -(alkyl)carboxy, -phosphonoalkyl, -alkylamino radicals, $C_2$- to $C_{20}$-alkenyl radicals or $C_6$- to $C_{20}$-aryl, -aryloxy, -hydroxyaryl, -arylcarboxy or -arylamino radicals which may be further substituted, q is an integer from 2 to 6 and r is an integer, wherein the alkylamino radicals mentioned may also be continued in the alkyl moiety in the manner of dendrimers and wherein the polyamine mentioned may also be quaternized at tertiary and/or free primary and/or secondary nitrogen atoms present or still present in the compounds (II).

The number r must be chosen in such a way that the average molar mass is within the specified range. Preferred ranges for the average molar mass ($M_W$) of the polyamines (IV) extend from 100 to 1,000,000 and particularly from 100 to 100,000. q is preferably 2.

Preferred meanings for $R^9$ to $R^{11}$ are again those specified above for $R^3$ to $R^8$.

Dendrimers or dendrimerlike amines or their precursors include N,N,N',N'-tetraminopropylethylenediamie, also known as N6-amine, and the dendrimeric amines preparable therefrom by aminopropylation and known as N14-, N30-, N62- and N128-amine according to the number of their nitrogen atoms. These amines have a basic ethylenediamine skeleton whose hydrogen atoms are substituted by amino (n-propyl) radicals on the nitrogen. The terminal amino groups may in turn be substituted by corresponding aminopropyl groups (N14-amine) etc. Methods for preparing these amines are described in WO 96/15097 starting from ethylenediamine. Likewise preferred examples of these amines are corresponding N-amines as described in WO 93/14147, which are prepared from butylenediamine instead of ethylenediamine as above.

In a further particularly preferred embodiment, Y is the radical of a polyvinylamine of the general formula (V)

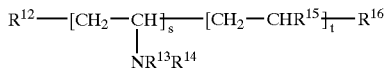

which has an average molar mass ($M_W$) of from 300 to 100,000,000 and wherein $R^{12}$ to $R^{16}$ are independently hydrogen, linear or branched $C_1$- to $C_{20}$-alkyl, -alkoxy, -polyoxyethylene, -hydroxyalkyl, -(alkyl)carboxy, -phosphonoalkyl, -alkylamino radicals, $C_2$- to $C_{20}$-alkenyl radicals or $C_6$- to $C_{20}$-aryl, -aryloxy, o-Hydroxybenzoyl Phthalimidoyl o-Carboxamidobenzoyl o-($C_1$- to $C_8$-Alkoxycarbonyl)benzoyl o-Aminobenzoyl o-(Mono-$C_1$- to $C_8$-alkylamino)benzoyl o-(Di-$C_1$- to $C_8$-alkylamino)benzoyl 2-Cyano-3,3-diphenylacryloyl m-Benzimidazolyl-p-hydroxybenzoyl Individual particularly preferred compounds (A) themselves are:

α,ω-Bis[(p-dimethylamino)benzoylamide] from N,N'-bis(3-aminopropyl)-1,2-ethylenediamine α,ω-Bis[(p-dimethylamino)benzoylamide] from triethylenetetramine α,ω-Bis[(p-dimethylamino)benzoylamide] from pentaethylenehexamine α, ω-Bis[p-methoxycinnamoylamide] from N,N'-bis(3-aminopropyl)-1,2-ethylenediamine quaternized at the two internal secondary amino groups by two methyl groups each α-(p-Methoxycinnamoylamide) from N,N'-bis(3-aminopropyl)-1,2-ethylenediamine α,ω-Bis[p-methoxycinnamoylamide] from pentaethylenehexamine α-(p-Dimethylamino)benzoylamide from N,N'-bis(3-aminopropyl)-1,2-ethylenediamine Reaction product of a polyethyleneimine of the formula (III) of $M_W$=700 with methyl p-methoxycinnamate in a molar ratio of 1:3

Reaction product of a polyethyleneimine of the formula (III) of $M_w$=700 with ethyl 2-cyano-3,3-diphenylacrylate in a molar ratio of 1:3.

Textile material for which the compounds (A) of the present invention have affinity and on which they are able to develop their protective action includes in particular clothing articles, i.e., textiles which are worn on the human skin, but also house and garden articles comprising dyed textiles such as awnings and sunshades which are exposed to intensive solar irradiation. This textile material to be protected preferably comprises cellulose (cotton), examples of textile materials of interest here being apparel textiles comprising cotton or cotton-polyester blends.

The present invention also provides a method of protecting human skin against harmful UV radiation, which comprises applying compounds (A) containing structural units of the general formula (I) to textile material in the course of textile finishing, i.e., in the course of the manufacture of the textiles.

The present invention further provides a method of protecting human skin against harmful UV radiation, which comprises applying compounds (A) containing structural units of the general formula (I) to textile material in the course of laundering and/or laundry pre- or aftertreatment.

The present invention further provides a method of protecting dyed textile material against fading, which comprises applying compounds (A) containing structural units of the general formula (I) to textile material in the course of textile finishing.

The present invention further provides a method of protecting dyed textile material against fading, which comprises applying compounds (A) containing structural units of the general formula (I) to textile material in the course of laundering and/or laundry pre- or aftertreatment.

The present invention further provides a method of increasing the UV protection factor (UPF) of textile material, which comprises applying compounds (A) containing structural units of the general formula (I) to textile material in the course of textile finishing i.e., in the course of the manufacture of the textiles.

The present invention further provides a method of increasing the UV protection factor (UPF) of textile material, which comprises applying compounds (A) containing structural units of the general formula (I) to textile material in the course of laundering and/or laundry pre- or aftertreatment.

The UV protection factor UPF of textiles is determined in accordance with the Australian/New Zealand standard AS/NZS 4399:1996 using an in vitro method. It measures the UV transmission of the textile object. The spectral transmission can be used to determine the protection factor directly using the following equation:

$$UPF = \frac{\int_{\lambda=280\text{ nm}}^{400\text{ nm}} S_\lambda \times E_\lambda \times d\lambda}{\int_{\lambda=280\text{ nm}}^{400\text{ nm}} S_\lambda \times E_\lambda \times T_\lambda \times d\lambda}$$

where
$S_\lambda$=spectral irradiation of the sun in the UV region at the wavelength $\lambda$
$E_\lambda$=spectral erythema action of the UV radiation at the wavelength $\lambda$
$T_\lambda$=spectral transmission of the textile object at the wavelength $\lambda$.

The UV absorbers (A) of the invention which possess fiber affinity and contain at least one structural unit (I) can be applied in the course of the finishing of the textile material, i.e., in the course of the manufacture of the textiles, or in the course of caring for the finished textile article, i.e., in the course of laundering and/or laundry pre- or aftertreatment.

By textile finishing are meant the operations carried out in the course of the manufacture of textiles to enhance the utility of the textiles and make them more attractive through advantageous manipulation of their external properties. Typical operations to enhance utility are easycare finishing, creaseproofing and shrinkproofing. Typical processes to enhance attractiveness are dyeing, bleaching, printing and mercerizing. The finishing of piece goods in particular generally involves the use of hand modifiers which include the finishing agents and to which the compounds (A) of the present invention are preferably likewise added.

The present invention also provides a laundry detergent comprising from 0.01 to 20% by weight, in particular from 0.1 to 10% by weight, especially from 0.1 to 5% by weight, of at least one compound (A) containing structural units of the general formula (I) as well as the other, customary ingredients.

The laundry detergent of the invention generally includes as other, customary ingredients
(B) from 1 to 60% by weight of inorganic builders based on crystalline or amorphous aluminosilicates, crystalline or amorphous silicates, carbonates or phosphates,
(C) from 0.5 to 40% by weight of anionic surfactants, and
(D) from 0.5 to 40% by weight of nonionic surfactants.

Suitable inorganic builders (B) are especially crystalline or amorphous aluminosilicates having ion-exchanging properties such as, in particular, zeolites. Various types of zeolite are suitable, especially zeolites A, X, B, P, MAP and HS in their sodium form or in forms in which sodium is partly replaced by other cations such as lithium, potassium, calcium, magnesium or ammonium. Suitable zeolites are described for example in EP-A 038591, EP-A 021491, EP-A 087035, U.S. Pat. No. 4,604,224, GB-A 2013259, EP-A 522726, EP-A 384070 and WO-A 94/24251.

Suitable crystalline silicates (B) are for example disilicates or sheet-silicates, for example $\delta$-$Na_2Si_2O_5$ or $\beta$-$Na_2Si_2O_5$ (SKS 6 or SKS 7 from Hoechst). The silicates can be used in the form of their alkali metal, alkaline earth metal or ammonium salts, preferably sodium, lithium and magnesium silicates.

Amorphous silicates such as, for example, sodium metasilicate, which has a polymeric structure, or amorphous disilicate (Britesil® H 20 from Akzo) are likewise useful.

Suitable inorganic builder substances (B) based on carbonate are carbonates and bicarbonates. These can be used in the form of their alkali metal, alkaline earth metal or ammonium salts. Preference is given to using sodium, lithium and magnesium carbonates or bicarbonates, especially sodium carbonate and/or sodium bicarbonate.

Customary phosphates useful as inorganic builders (B) are polyphosphates, such as, for example, pentasodium triphosphate.

The components (B) mentioned can be used singly or mixed with each or one another.

The component (B) is preferably present in the laundry detergent of the invention in an amount from 5 to 50% by weight, especially from 10 to 45% by weight.

In a preferred embodiment, the laundry detergent of the invention includes no phosphate-based builders or not more than 5% by weight, especially not more than 2% by weight, of phosphate-based builders.

Suitable anionic surfactants (C) are for example fatty alcohol sulfates of fatty alcohols containing from 8 to 22, preferably from 10 to 18, carbon atoms, e.g., $C_9$- to $C_{11}$-alcohol sulfates, $C_{12}$- to $C_{14}$-alcohol sulfates, $C_{12}$–$C_{18}$-alcohol sulfates, lauryl sulfate, cetyl sulfate, myristyl sulfate, palmityl sulfate, stearyl sulfate and tallow alcohol sulfate.

Further suitable anionic surfactants are sulfated ethoxylated $C_8$- to $C_{22}$-alcohols (alkyl ether sulfates) and their soluble salts. Compounds of this kind are prepared for example by first alkoxylating a $C_8$- to $C_{22}$-alcohol, preferably a $C_{10}$- to $C_{18}$-alcohol, for example a fatty alcohol, and subsequently sulfating the alkoxylation product. The alkoxylation is preferably carried out using ethylene oxide, from 1 to 50, preferably from 1 to 20, mol of ethylene oxide being used per mole of alcohol. However, the alkoxylation of the alcohols can also be effected with propylene oxide alone and optionally butylene oxide. Also suitable are those alkoxylated $C_8$- to $C_{22}$-alcohols which contain ethylene oxide and propylene oxide or ethylene oxide and butylene oxide or ethylene oxide and propylene oxide and butylene oxide. The alkoxylated $C_8$- to $C_{22}$-alcohols can contain the ethylene oxide, propylene oxide and butylene oxide units in the form of blocks or in random distribution. Depending on the type of alkoxylation catalyst, alkyl ether sulfates can be obtained with broad or narrow alkylene oxide homolog distribution.

Further suitable anionic surfactants are alkanesulfonates such as $C_8$- to $C_{24}$-alkanesulfonates, preferably $C_{10}$- to $C_{18}$-alkanesulfonates, and also soaps such as, for example, the sodium and potassium salts of $C_8$- to $C_{24}$-carboxylic acids.

Further suitable anionic surfactants are linear $C_8$- to $C_{20}$-alkylbenzenesulfonates ('LAS'), preferably linear $C_9$- to $C_{13}$-alkylbenzenesulfonates and -alkyltoluenesulfonates.

Useful anionic surfactants (C) further include $C_8$- to $C_{24}$-olefinsulfonates and -disulfonates, which may also be mixtures of alkene- and hydroxyalkane-sulfonates and -disulfonates, respectively, alkyl ester sulfonates, sulfonated polycarboxylic acids, alkylglycerolsulfonates, fatty acid glyceryl ester sulfonates, alkylphenol polyglycol ether sulfates, paraffinsulfonates containing from about 20 to about 50 carbon atoms (based on paraffin or paraffin mixtures obtained from natural sources), alkyl phosphates, acyl isethionates, acyl taurates, acyl methyltaurates, alkylsuccinic acids, alkenylsuccinic acids or their monoesters or monoamides, alkylsulfosuccinic acids or their amides, mono- and diesters of sulfosuccinic acids, acyl sarcosinates, sulfated alkylpolyglucosides, alkylpolyglycol carboxylates and also hydroxyalkyl sarcosinates.

The anionic surfactants are preferably included in the laundry detergent in the form of salts. Suitable cations in these salts are alkali metal ions such as sodium, potassium and lithium and ammonium salts, for example hydroxyethylammonium, di(hydroxyethyl)ammonium and tri(hydroxyethyl)ammonium salts.

The component (C) is preferably present in the laundry detergent of the invention in an amount of from 1 to 30% by weight, in particular from 3 to 25% by weight, especially from 5 to 15% by weight. If linear $C_9$- to $C_{20}$-alkylbenzenesulfonates (LAS) are used, they are customarily used in an amount of up to 10% by weight, especially up to 8% by weight.

It is possible to use individual anionic surfactants or a combination of different anionics. It is possible to use anionic surfactants from just one class, for example just fatty alcohol sulfates or just alkylbenzenesulfonates, but it is also possible to use surfactant mixtures from different classes, for example a mixture of fatty alcohol sulfates and alkylbenzenesulfonates.

Examples of suitable nonionic surfactants (D) are alkoxylated $C_8$-to $C_{22}$-alcohols such as fatty alcohol alkoxylates or oxo alcohol alkoxylates. The alkoxylation can be carried out with ethylene oxide, propylene oxide and/or butylene oxide. Useful surfactants include all alkoxylated alcohols which contain at least two molecules of an aforementioned alkylene oxide after an addition reaction. Here too block polymers of ethylene oxide, propylene oxide and/or butylene oxide are suitable or addition products which contain the alkylene oxides mentioned in random distribution. The amount of alkylene oxide used per mole of alcohol is generally within the range from 2 to 50, preferably from 3 to 20, mol of at least one alkylene oxide. The preferred alkylene oxide is ethylene oxide. The alcohols preferably have from 10 to 18 carbon atoms. Depending on the type of alkoxylation catalyst, alkoxylates can be obtained with broad or narrow alkylene oxide homolog distribution.

A further class of suitable nonionic surfactants are alkylphenol alkoxylates such as alkylphenol ethoxylates containing $C_6$- to $C_{14}$-alkyl chains and from 5 to 30 mol of alkylene oxide units.

Another class of nonionic surfactants are alkylpolyglucosides having from 8 to 22, preferably from 10 to 18, carbon atoms in the alkyl chain. These compounds usually contain from 1 to 20, preferably from 1.1 to 5, glucoside units.

Another class of nonionic surfactants are N-alkylglucamides of the general structures

where $B_1$ is $C_6$- to $C_{22}$-alkyl, $B^2$ is hydrogen or $C_1$- to $C_4$-alkyl and D is a polyhydroxyalkyl radical containing from 5 to 12 carbon atoms and at least 3 hydroxyl groups. Preferably, $B^1$ is $C_{10}$- to $C_{18}$-alkyl, $B^2$ is $CH_3$ and D is a $C_5$ or $C_6$ radical. Such compounds are obtained for example by acylating reductively aminated sugars with acyl chlorides of $C_{10}$- to $C_{18}$-carboxylic acids.

Further suitable nonionic surfactants are the end group capped fatty acid amide alkoxylates known from WO-A 95/11225 which have the general formula

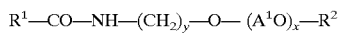

where
$R^1$ is $C_5$- to $C_{21}$-alkyl or -alkenyl,
$R^2$ is $C_1$- to $C_4$-alkyl,
$A^1$ is $C_2$- to $C_4$-alkylene,
y is 2 or 3, and
x is from 1 to 6.

Examples of such compounds are the reaction products of n-butyltriglycolamine of the formula $H_2N-(CH_2-CH_2-O)_3-C_4H_9$ with methyl dodecanoate or the reaction products of ethyltetraglycolamine of the formula $H_2N-(CH_2-CH_2-O)_4-C_2H_5$ with a commercially available mixture of saturated methyl esters of $C_8$- to $C_{18}$-fatty acids.

Useful nonionic surfactants (D) further include block copolymers of ethylene oxide, propylene oxide and/or butylene oxide (Pluronic® and Tetronic® products from BASF), polyhydroxy or polyalkoxy fatty acid derivatives such as polyhydroxy fatty acid amides, N-alkoxy- or N-aryloxypolyhydroxy fatty acid amides, fatty acid amide ethoxylates, especially end group capped ones, and also fatty acid alkanolamide alkoxylates.

The component (D) is preferably present in the laundry detergent of the invention in an amount of from 1 to 30% by weight, especially from 3 to 25% by weight, in particular from 5 to 20% by weight.

Individual nonionic surfactants or a combination of different nonionics can be used. It is possible to use nonionic surfactants from just one class, especially just alkoxylated $C_8$- to $C_{22}$-alcohols, but it is also possible to use surfactant mixtures from different classes.

In a preferred embodiment, the laundry detergent of the invention, in addition to the inorganic builders (B), includes from 0.05 to 20% by weight, especially from 1 to 10% by weight, of organic cobuilders in the form of low molecular weight, oligomeric or polymeric carboxylic acids, especially polycarboxylic acids, or phosphonic acids or their salts, especially sodium or potassium salts.

Examples of low molecular weight carboxylic acids or phosphonic acids useful as organic cobuilders are:

phosphonic acids, such as for example 1-hydroxyethane-1, 1-diphosphonic acid, aminotris(methylenephosphonic acid), ethylenediaminetetra(methylenephosphonic acid), hexamethylenediaminetetra(methylenephosphonic acid) and diethylenetriaminepenta (methylenephosphonic acid);

$C_4$- to $C_{20}$-di-, -tri- and -tetracarboxylic acids such as for example succinic acid, propanetricarboxylic acid, butanetetracarboxylic acid, cyclopentanetetracarboxylic acid and alkyl and alkenylsuccinic acids having $C_2$- to $C_{16}$-alkyl or -alkenyl moieties;

$C_4$- to $C_{20}$-hydroxycarboxylic acids such as for example malic acid, tartaric acid, gluconic acid, glutaric acid, citric acid, lactobionic acid and sucrose mono-, -di- and tricarboxylic acid;

aminopolycarboxylic acids such as for example nitrilotriacetic acid, β-alaninediacetic acid, ethylenediaminetetraacetic acid, serinediacetic acid, isoserinediacetic acid, alkylethylene-diaminetriacetates, N,N-bis (carboxymethyl)glutamic acid, ethylenediaminedisuccinic acid and N-(2-hydroxyethyl)imino-diacetic acid, methyl- and ethyl-glycinediacetic acid.

Examples of oligomeric or polymeric carboxylic acids useful as organic cobuilders are:

oligomaleic acids as described for example in EP-A 451508 and EP-A 396303;

co- and terpolymers of unsaturated $C_4$–$C_8$-dicarboxylic acids which may contain copolymerized units derived from monoethylenically unsaturated comonomers of the group (i) in amounts of up to 95% by weight,
of the group (ii) in amounts of up to 60% by weight, and
of the group (iii) in amounts of up to 20% by weight.

Examples of unsaturated $C_4$–$C_8$-dicarboxylic acids useful here include maleic acid, fumaric acid, itaconic acid and citraconic acid. Maleic acid is preferred.

The group (i) consists of monoethylenically unsaturated $C_3$–$C_8$-monocarboxylic acids, for example acrylic acid, methacrylic acid, crotonic acid and vinylacetic acid. Preferred members of group (i) are acrylic acid and methacrylic acid.

Group (ii) consists of monoethylenically unsaturated $C_2$–$C_{22}$-olefins, vinyl alkyl ethers having $C_1$–$C_8$-alkyl groups, styrene, vinyl esters of $C_1$–$C_8$-carboxylic acids, (meth)acrylamide and vinylpyrrolidone. Preference in group (ii) is given to $C_2$–$C_6$-olefins, vinyl alkyl ethers containing $C_1$–$C_4$-alkyl groups, vinyl acetate and vinyl propionate.

Group (iii) consists of (meth)acrylic esters of $C_1$- to $C_8$-alcohols, (meth)acrylonitrile, (meth)acrylamides of $C_1$–$C_8$-amines, N-vinylformamide and N-vinylimidazole.

If the polymers of group (ii) contain units derived from vinyl esters, these units may also be partly or wholly hydrolyzed into vinyl alcohol units. Suitable co- and terpolymers are known for example from U.S. Pat. No. 3,887,806 and DE-A 4313909.

Copolymers of dicarboxylic acids useful as organic cobuilders are preferably:
copolymers of maleic acid and acrylic acid in a weight ratio of from 10:90 to 95:5, particularly preferably those in a weight ratio of from 30:70 to 90:10 with molar masses from 1000 to 150,000;
terpolymers of maleic acid, acrylic acid and a vinyl ester of a $C_1$–$C_3$-carboxylic acid in a weight ratio of from 10 (maleic acid): 90 (acrylic acid+vinyl ester) to 95 (maleic acid): 10 (acrylic acid+vinyl ester), the weight ratio of acrylic acid to vinyl ester being within the range from 30:70 to 70:30;
copolymers of maleic acid with $C_2$–$C_8$-olefins in a molar ratio of from 40:60 to 80:20, of which copolymers of maleic acid with ethylene, propylene or isobutene in a molar ratio of 50:50 are particularly preferred.

Graft polymers of unsaturated carboxylic acids on low molecular weight carbohydrates or hydrogenated carbohydrates, cf. U.S. Pat. No. 5,227,446, DE-A 4415623 and DE-A 4313909, are likewise useful as organic cobuilders.

Examples of useful unsaturated carboxylic acids here are maleic acid, fumaric acid, itaconic acid, citraconic acid, acrylic acid, methacrylic acid, crotonic acid and vinylacetic acid and also mixtures of acrylic acid and maleic acid which are grafted on in amounts of from 40 to 95% by weight, based on the component to be grafted.

The graft copolymer may additionally include, by way of modification, up to 30% by weight, based on the component to be grafted, of further monoethylenically unsaturated monomers in polymerized form. Suitable modifying monomers are the abovementioned monomers of groups (ii) and (iii).

Useful grafting bases include degraded polysaccharides, for example acidic or enzymatically degraded starches, inulins or cellulose, protein hydrolyzates and reduced (hydrogenated or reductively aminated) degraded polysaccharides, for example mannitol, sorbitol, aminosorbitol and N-alkylglucamine, and also polyalkylene glycols having molar masses of up to $M_W$=5000, for example polyethylene glycols, ethylene oxide/propylene oxide or ethylene oxide/butylene oxide or ethylene oxide/propylene oxide/butylene oxide block copolymers and alkoxylated mono- or polyhydric $C_1$–$C_{22}$-alcohols; cf. U.S. Pat. No. 5,756,456.

Polyglyoxylic acids useful as organic cobuilders are described for example in EP-B 001004, U.S. Pat. No. 5,399,286, DE-A 4106355 and EP-A 656914. The end groups of the polyglyoxylic acids can have different structures.

Polyamidocarboxylic acids and modified polyamidocarboxylic acids useful as organic cobuilders are known for example from EP-A 454126, EP-B 511037, WO-A 94/01486 and EP-A 581452.

Useful organic cobuilders also include in particular polyaspartic acids or cocondensates of aspartic acid with further amino acids, $C_4$–$C_{25}$-mono- or -dicarboxylic acids and/or $C_4$–$C_{25}$-mono- or -diamines. Particular preference is given to polyaspartic acids prepared in phosphorus-containing acids and modified with $C_6$–$C_{22}$-mono- or -dicarboxylic acids or with $C_6$–$C_{22}$-mono- or diamines.

Useful organic cobuilders further include iminodisuccinic acid, oxydisuccinic acid, aminopolycarboxylates, alkylpolyamino-carboxylates, aminopolyalkylenephosphonates, polyglutamates, hydrophobic modified citric acid, e.g., agaricic acid, poly-α-hydroxyacrylic acid, N-acylethylenediaminetriacetates such as lauroylethylenediaminetriacetate and alkylamides of ethylenediaminetetraacetic acid such as EDTA-tallowamide.

It is also possible to use oxidized starches as organic cobuilders.

In a further preferred embodiment, the laundry detergent of the invention, as well as in particular the inorganic builders (B), the anionic surfacts (C) and/or the nonionic surfactants (D), further includes from 0.5 to 20% by weight, especially from 1 to 10% by weight, of glycine-N,N-diacetic acid derivatives as described in WO 97/19159.

In a further preferred embodiment, the laundry detergent of the invention further comprises from 0.5 to 30% by weight, especially from 5 to 27% by weight, in particular from 10 to 23% by weight, of bleaching agents in the form of percarboxylic acids, e.g., diperoxodecanedicarboxylic acid, phthalimidopercaproic acid or monoperoxophthalic acid or -terephthalic acid, adducts of hydrogen peroxide with inorganic salts, for example sodium perborate monohydrate, sodium perborate tetrahydrate, sodium carbonate perhydrate or sodium phosphate perhydrate, adducts of hydrogen peroxide with organic compounds, for example urea perhydrate, or of inorganic peroxo salts, for example alkali metal persulfates, or alkali metal peroxodisulfates, optionally in combination with from 0 to 15% by weight, preferably from 0.1 to 15% by weight, especially from 0.5 to 8% by weight, of bleach activators. In the case of color detergents, the bleaching agent (if present) is generally used without bleach activator; in other cases, bleach activators are usually present.

Useful bleach activators include:
polyacylated sugars, for example pentaacetylglucose;
acyloxybenzenesulfonic acids and their alkali metal and alkaline earth metal salts, for example sodium p-nonanoyloxybenzenesulfonate or sodium p-benzoyloxybenzenesulfonate;
N,N-diacylated and N,N,N',N'-tetraacylated amines, for example N,N,N',N'-tetraacetylmethylenediamine and -ethylenediamine (TAED), N,N-diacetylaniline, N,N-diacetyl-p-toluidine or 1,3-diacylated hydantoins such as 1,3-diacetyl-5,5-dimethylhydantoin;
N-alkyl-N-sulfonylcarboxamides, for example N-methyl-N-mesylacetamide or N-methyl-N-mesylbenzamide;
N-acylated cyclic hydrazides, acylated triazoles or urazoles, for example monoacetylmaleic hydrazide;
O,N,N-trisubstituted hydroxylamines, for example O-benzoyl-N,N-succinylhydroxylamine, O-acetyl-N,N- succinylhydroxylamine or O,N,N-triacetylhydroxylamine;

N,N'-diacylsulfurylamides, for example N,N'-dimethyl-N,N'-diacetylsulfurylamide or N,N'-diethyl-N,N'-dipropionylsulfurylamide;

acylated lactams such as, for example, acetylcaprolactam, octanoylcaprolactam, benzoylcaprolactam or carbonylbiscaprolactam;

anthranil derivatives such as, for example, 2-methylanthranil or 2-phenylanthranil;

triacyl cyanurates, for example triacetyl cyanurate or tribenzoyl cyanurate;

oxime esters and bisoxime esters, for example O-acetylacetone oxime or bisisopropyl iminocarbonate;

carboxylic anhydrides, for example acetic anhydride, benzoic anhydride, m-chlorobenzoic anhydride or phthalic anhydride;

enol esters, for example isopropenyl acetate;

1,3-diacyl-4,5-diacyloxyimidazolines, for example 1,3-diacetyl-4,5-diacetoxyimidazoline;

tetraacetylglycoluril and tetrapropionylglycoluril;

diacylated 2,5-diketopiperazines, for example 1,4-diacetyl-2,5-diketopiperazine;

ammonium-substituted nitriles, for example N-methylmorpholiniumacetonitrize methylsulfate;

acylation products of propylenediurea and 2,2-dimethylpropylenediurea, for example tetraacetylpropylenediurea;

α-acyloxypolyacylmalonamides, for example α-acetoxy-N,N'-diacetylmalonamide;

diacyldioxohexahydro-1,3,5-triazines, for example 1,5-diacetyl-2,4-dioxohexahydro-1,3,5-triazine;

benz (4H)-1,3-oxazin-4-ones having alkyl radicals, for example methyl, or aromatic radicals, for example phenyl, in position 2.

The described bleaching system comprising bleaching agents and bleach activators may optionally include bleach catalysts as well. Examples of suitable bleach catalysts are quaternized imines and sulfoneimines, which are described for example in U.S. Pat. No. 5,360,569 and EP-A 453 003. Particularly effective bleach catalysts are manganese complexes, which are described for example in WO-A 94/21777. When used, such compounds are incorporated in laundry detergents in amounts up to 1.5% by weight, especially up to 0.5% by weight, and in the case of very active manganese complexes, in amounts up to 0.1% by weight.

In addition to the described bleaching system comprising bleaching agents, bleach activators and optionally bleach catalysts, it is also possible for the laundry detergent of the invention to utilize systems involving enzymatic peroxide release or photoactivated bleaching systems.

In a further preferred embodiment, the laundry detergent of the invention additionally includes from 0.05 to 4% by weight of enzymes. Preferred laundry-detergent enzymes are proteases, amylases, lipases and cellulases. The enzymes are used in amounts which are preferably from 0.1 to 1.5% by weight, particularly preferably from 0.2 to 1.0% by weight, of the formulated enzyme. Examples of suitable proteases are Savinase and Esperase (from Novo Nordisk). An example of a suitable lipase is Lipolase (from Novo Nordisk). An example of a suitable cellulose is Celluzym (from Novo Nordisk). The use of peroxidases to activate the bleach system is also possible. Individual enzymes or a combination of different enzymes can be used. If desired, the laundry detergent of the invention may additionally include enzyme stabilizers, for example calcium propionate, sodium formate or boric acids or salts thereof, and/or antioxidants.

In addition to the main components heretofore mentioned, the laundry detergent of the invention may also include the following further customary additives in the amounts customary for this purpose:

cationic surfactants, customarily in an amount of up to 25% by weight, preferably from 3 to 15% by weight, for example $C_8$- to $C_{16}$-dialkyldimethylammonium halides, dialkoxydimethylammonium halides or imidazolinium salts with long-chain alkyl;

amphoteric surfactants, customarily in an amount of up to 15% by weight, preferably from 2 to 10% by weight, for example derivatives of secondary or tertiary amines, for example $C_{12}$–$C_{18}$-alkylbetaines or $C_{12}$–$C_{18}$-alkylsulfobetaines or amine oxides such as alkyldimethylamine oxides;

soil antiredeposition agents and soil release polymers (these are for example polyesters of polyethylene oxides with ethylene glycol and/or propylene glycol and aromatic dicarboxylic acids or aromatic and aliphatic dicarboxylic acids or polyesters of unilaterally end group capped polyethylene oxides with di- and/or more highly hydric alcohols and dicarboxylic acids. Such polyesters are known, cf. for example U.S. Pat. No. 3,557,039, GB-A-1 154 730, EP-A-0 185 427, EP-A-0 241 984, EP-A-0 241 985, EP-A-0 272 033 and U.S. Pat. No. 5,142,020. Further suitable soil release polymers are amphiphilic graft polymers or copolymers of vinyl ester and/or acrylic ester on polyalkylene oxides, cf. U.S. Pat. No. 4,746,456, U.S. Pat. No. 4,846,995, DE-A-3 711 299, U.S. Pat. No. 4,904,408, U.S. Pat. No. 4,846,994 and U.S. Pat. No. 4,849,126, or modified celluloses, for example methylcellulose, hydroxypropylcellulose, or carboxymethylcellulose. Soil antiredeposition agents and soil release polymers are present in the laundry detergents at from 0.1 to 2.5% by weight, preferably at from 0.2 to 1.5% by weight, particularly preferably at from 0.3 to 1.2% by weight. Preferred soil release polymers are the graft polymers of vinyl acetate on polyethylene oxide of molar mass 2500–8000 in a weight ratio of from 1.2:1 to 3.0:1 known from U.S. Pat. No. 4,746,456, and also commercially available polyethylene terephthalate/polyoxyethylene terephthalates of molar mass 3000–25,000 from polyethylene oxides of molar mass 750–5000 with terephthalic acid and ethylene oxide and a molar ratio of polyethylene terephthalate to polyoxyethylene terephthalate of from 8:1 to 1:1 and the block polycondensates known from DE-A-44 03 866 which contain blocks of (a) ester units of polyalkylene glycols having a molar mass of from 500 to 7500 and aliphatic dicarboxylic acids and/or monohydroxymonocarboxylic acids and (b) ester units of aromatic dicarboxylic acids and polyhydric alcohols. These amphiphilic block copolymers have molar masses of from 1500 to 25,000.);

color transfer inhibitors, for example home- and copolymers of N-vinylpyrrolidone, of N-vinylimidazole, of N-vinyloxazolidone or of 4-vinylpyridine N-oxide with molar masses of from 15,000 to 100,000 and also crosslinked finely divided polymers based on these monomers and having a particle size of from 0.1 to 500, preferably from 0.1 to 250, $\mu$m;

nonsurfactant foam suppressants or foam inhibitors, for example organopolysiloxanes and mixtures thereof with microfine, optionally silanized silica and also paraffins, waxes, microwaxes and mixtures thereof with silanized silica;

complexing agents (also as organic cobuilders);
optical brighteners;
polyethylene glycols;
perfumes or fragrances;
fillers;
inorganic extenders, for example sodium sulfate;
formulation assistants;
solubility improvers;
opacifiers and pearlizers;
dyes,
corrosion inhibitors;
peroxide stabilizers;
electrolytes.

A solid laundry detergent according to the invention is customarily in powder or granule form or in the form of extrudates or tablets.

Pulverulent or granular laundry detergents according to the invention may include up to 60% by weight of inorganic extenders.

Sodium sulfate is usually used for this purpose. However, the extender content of the laundry detergents according to the invention is preferably low, only up to 20% by weight, particularly preferably only up to 8% by weight, especially in the case of compacts or ultracompacts. The solid laundry detergents of the invention may have various bulk densities in the range from 300 to 1300 g/l, especially within the range from 550 to 1200 g/l. Modern compacts generally have high bulk densities and a granular construction. To achieve the desired compaction of the detergents, it is possible to use the techniques customary in the art.

The laundry detergent of the invention is produced and optionally finished in a conventional manner.

The present invention further provides a laundry pre- and aftertreatment comprising from 0.01 to 40% by weight, especially from 0.5 to 20% by weight, of at least one compound (A) containing structural units of the formula (I) as well as the other, customary ingredients.

Preference is here given to a textile pre- and aftertreatment further comprising from 1 to 50% by weight, especially from 3 to 30% by weight, of one or more cationic surfactants selected from the group consisting of quaternary diesterammonium salts, quaternary tetraalkylammonium salts, quaternary diamidoammonium salts, amidoamino esters and imidazolinium salts.

Quaternary diesterammonium salts are especially those which have two $C_{11}$- to $C_{22}$-alk(en)ylcarbonyloxy(mono- to pentamethylene) radicals and two $C_1$- to $C_3$-alkyl or hydroxyalkyl radicals on the quaternary nitrogen atom and, for example, chloride, bromide, methosulfate or sulfate as counterion.

Quaternary diesterammonium salts further include in particular those which have a $C_{11}$- to $C_{22}$-alk(en)ylcarbonyloxytrimethylene radical bearing a $C_{11}$- to $C_{22}$-alk(en)ylcarbonyloxy radical on the central carbon atom of the trimethylene group and three $C_1$- to $C_3$-alkyl or -hydroxyalkyl radicals on the quaternary nitrogen atom and, for example, chloride, bromide, methosulfate or sulfate as counterion.

Quaternary tetraalkylammonium salts are in particular those which have two $C_1$- to $C_6$-alkyl radicals and two $C_8$- to $C_{24}$-alk(en)yl radicals on the quaternary nitrogen atom and, for example, chloride, bromide, methosulfate or sulfate as counterion.

Quaternary diamidoammonium salts are in particular those which bear two $C_8$- to $C_{24}$-alk(en)ylcarbonylaminoethylene radicals, a substituent selected from hydrogen, methyl, ethyl and polyoxyethylene having up to 5 oxyethylene units and as fourth radical a methyl group on the quaternary nitrogen atom and, for example, chloride, bromide, methosulfate or sulfate as counterion.

Amidoamino esters are in particular tertiary amines bearing a $C_{11}$- to $C_{22}$-alk(en)ylcarbonylamino(mono- to trimethylene) radical, a $C_{11}$- to $C_{22}$-alk(en)ylcarbonyloxy (mono- to trimethylene) radical and a methyl group as substituents on the nitrogen atom.

Imidazolinium salts are in particular those which bear a $C_{14}$- to $C_{18}$-alk(en)yl radical in position 2 of the heterocycle, a $C_{14}$- to $C_{18}$-alk(en)ylcarbonyl(oxy or amino)ethylene radical on the neutral nitrogen atom and hydrogen, methyl or ethyl on the nitrogen atom carrying the positive charge, while counterions here are for example chloride, bromide, methosulfate or sulfate.

Contemplated laundry aftertreatments are in particular fabric softeners for application in the final rinse and in the course of fabric care.

Other customary ingredients for such a textile pre- and aftertreatment are nonionic surfactants, fragrances, dyes, stabilizers, fiber and color protection additives, viscosity modifiers, soil release additives, corrosion inhibitors, bactericides, preservatives and water in the customary amounts.

Some of the compounds (A) are novel substances. The present invention accordingly also provides compounds (A') conforming to the general formula (IIa)

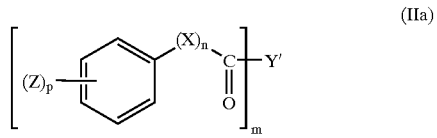

(IIa)

where
Y' is the radical of an aliphatic, cycloaliphatic, aromatic or mixed aliphatic-aromatic group which has an average molar mass ($M_W$) of up to 100,000,000, which contains at least m' primary and/or secondary amino groups or together at least m' primary and/or secondary amino groups and hydroxyl groups capable of forming amide or ester bonds with the structural unit (I) and which may also be quaternized at tertiary and/or free primary and/or secondary nitrogen atoms present or still present in the compounds (IIa),
m' is from 1 to 200, subject to the provisos that the number m of the structural units (I) accounts for from 10 to 100% of m' and that, however, at least one structural unit (I) is present in the compounds (II),
and X, Z, n and p are each as defined above.

The compounds (A') as well as the compounds (A) are advantageously prepared by reacting carboxylic acid derivatives of the general formula (Ia)

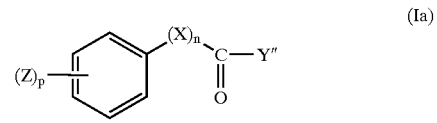

(Ia)

where Y" is an alkyl group having from 1 to 4 carbon atoms, for example methyl or ethyl, a halogen atom, for example chlorine or bromine, an amino group optionally bearing one or two $C_1$- to $C_4$-alkyl groups or a hydroxyl group and the other variables are each as defined above, with the parent compounds of Y' to form the corresponding carboxamide and/or carboxylic ester structures and then optionally quaternizing some or all of the tertiary and/or primary and/or secondary nitrogen atoms present or still present fig in the compounds (IIa).

The novel UV absorbers possessing affinity for textile fiber are highly useful on textile material not only to protect the human skin against harmful UV radiation but also to protect dyed textile material against fading. Textile material comprising at least one compound (A) containing at least one structural unit of the general formula (I) thus likewise forms part of the subject-matter of the present invention.

The Examples hereinbelow are intended to more particularly describe the invention without, however, limiting it.

EXAMPLE 1

Preparation of α,ω-bis[p-methoxycinnamoylamide] from N,N'-bis(3-aminopropyl)-1,2-ethylenediamine The following method of preparation is a typical example of how the compounds (A) are prepared: 28.8 g (0.15 mol) of methyl p-methoxycinnamate were heated together with 1.5 g (0.008 mol) of a 30% strength by weight solution of sodium methoxide in methanol and 13.2 g (0.075 mol) of N,N'-bis(3-aminopropyl)-1,2-ethylenediamine at 100° C. for 4 hours. The methanol was then distilled off. A customary workup afforded a pale beige product in a yield of 78%.

EXAMPLE 2

Quaternization of the Product of Example 1

The product of Example 1 was methylated at the two internal secondary amino groups in a conventional manner by reaction with dimethyl sulfate as methylating agent in a molar ratio of 1:4 to give a pale beige product in a yield of 98%.

Application tests

EXAMPLE 3

Application in Wash Cycle

Woven white cotton fabric having a basis weight of 100 g/m² and a UV protection factor UPF of 4.50 was washed at 60° C. for 30 minutes in the presence of water hardness of 3 mmol/l. The detergent used was a commercially available formulation (Persil® Megaperls Color) in a dosage of 4500 ppm, based on the wash liquor. The formulation included either no UV absorber having affinity for textile fiber or 400 ppm in each case, based on the wash liquor, of the novel UV absorber A1, A2 or A3, added before the wash. The fit 20 UV protection factor UPF was determined after the cotton fabrics had been washed, rinsed, spun and dried.

Structures of UV absorbers used:
A1=α,ω-bis[p-methoxycinnamoylamide] from pentaethylenehexamine
A2=reaction product of a commercially available polyethyleneimine of the formula (III) with $M_W$=700 (Polymin G 10 from BASF Aktiengesellschaft) with methyl p-methoxycinnamate in a molar ratio of 1:3
A3=α,ω-bis[p-methoxycinnamoylamide] from N,N'-bis(3-amino-propyl)-1,2-ethylenediamine quaternized with two methyl groups at both internal secondary amino groups (product of Example 2)

Table 1 shows the results of the tests:

TABLE 1

| | |
|---|---|
| without UV absorber | UPF = 4.60 |
| with UV absorber A1 | UPF = 11.30 |
| with UV absorber A2 | UPF = 10.00 |
| with UV absorber A3 | UPF = 11.70 |

The results show that the use of the UV absorbers A1 to A3 in the laundry wash cycle according to the present invention leads to a distinct increase in the textile UV protection.

EXAMPLE 4

Use as Laundry Aftertreatment in Final Rinse

Woven white cotton fabric having a basis weight of 100 g/m² and a UV protection factor UPF=4.50 was washed five times in succession. One wash consisted of a wash cycle at 40° C. with a commercially available detergent (Persil® Megaperls Color) and a subsequent final rinse. A commercially available final rinse fabric conditioner (Lenor® ultra) was used in a dose of 1000 ppm, based on the liquor. The fabric conditioner included either no UV absorber possessing affinity for textile fiber or in each case 100 ppm, based on the liquor, of the novel UV absorber A1, A2 or A3 (see Example 3), added before the final rinse. After each final rinse, a fabric sample was removed and its UV protection factor UPF was determined in the dried state.

Table 2 shows the results of the tests:

TABLE 2

| | after 1st wash | after 3rd wash | after 5th wash |
|---|---|---|---|
| without UV absorber | UPF = 4.81 | UPF = 5.09 | UPF = 5.05 |
| with UV absorber A1 | UPF = 12.48 | UPF = 18.50 | UPF = 23.85 |
| with UV absorber A2 | UPF = 10.76 | UPF = 24.88 | UPF = 31.42 |
| with UV absorber A3 | UPF = 10.93 | UPF = 20.17 | UPF = 31.92 |

It is clear that using the novel UV absorbers A1 to A3 increases the UV protection factor UPF of the cotton fabric as the number of washes increases. After just the 5th wash, the protection factors obtained show good to very good skin protection against UV radiation. The results further show that the textile protection against UV radiation is not improved when UV absorbers are absent.

We claim:
1. A method of treating textile fibers, comprising:
imparting UV light protection properties to textile fibers by treating the textile fibers with a compound having UV light absorption properties that contains at least one structural unit of formula (II)

$$\left[(Z)_p\underset{}{\underbrace{\phantom{XXXX}}}(X)_n-\underset{\underset{O}{\|}}{C}-Y\right]_m \quad (II)$$

and that adheres to the textile fibers, wherein
X is a group of the formula —$CR^1$=$CR^2$— or a carbonyl group C=O, where $R^1$ and $R^2$ are independently hydrogen, $C_1$- to $C_8$-alkyl, $C_1$- to $C_8$-alkoxy, $C_1$- to $C_8$-alkoxycarbonyl, $C_1$- to $C_8$-acyloxy, carboxyl, cyano, nitro, fluorine, chlorine, bromine, sulfonyl, $C_1$- to $C_8$-alkylsulfonyl or phenyl which may be substituted by up to 3 radicals selected from the group consisting of $C_1$- to $C_8$-alkyl, $C_1$- to $C_8$-alkoxy, $C_1$- to $C_8$-alkoxycarbonyl, $C_1$- to $C_8$-acyloxy, carboxyl, cyano, nitro, chlorine, bromine, sulfonyl and $C_1$- to $C_8$-alkylsulfonyl, where $R^1$ optionally is the group —NQ—CO—, which is bonded with its carbonyl carbon atom to the ortho position of the adjacent phenyl ring to form a benzopyrrolidone system, and in which Q is hydrogen or a $C_1$–$C_8$-alkyl radical;

Z is a substituent selected from the group consisting of $C_1$- to $C_8$-alkyl, $C_1$- to $C_8$ alkoxy, $C_1$- to $C_8$-alkoxycarbonyl, $C_1$- to $C_8$-acyloxy, carboxyl, cyano, nitro, fluorine, chlorine, bromine, sulfonyl, $C_1$- to $C_8$-alkylsulfonyl, amino, mono- or di-$C_1$- to $C_8$-alkylamino, carboxamido (with or without one or two $C_1$- to $C_8$-alkyl groups on the amide nitrogen), hydroxyl and saturated or unsaturated five- and six-membered heterocyclic radicals, which may be benzofused, and any two adjacent Z substituents may also form a saturated or unsaturated five- or six-membered ring, and in the case of p=0 an ortho-disposed carboxyl group may be combined with the carbonyl group present and a nitrogen atom attached directly to this carbonyl group to form a cyclic imide;

n is 0, 1, 2 or 3 and p is 0, 1, 2, 3, 4 or 5;

Y is the radical of an aliphatic, cycloaliphatic, or mixed aliphatic-aromatic group which has at least m' primary and/or secondary amino groups, m' hydroxyl groups or together at least m' primary and/or secondary amino groups and hydroxyl groups, which is capable of forming amide or ester bonds with the structural unit of the formula (I)

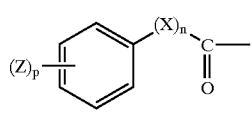

(I)

and the tertiary and/or free primary and/or secondary nitrogen atoms present in the compounds of radical Y optionally being quaternized; and m is the number of structural units (I) bonded to primary and/or secondary amino groups and hydroxyl groups and accounts for from 10 to 100% of the number of these m' groups which range from 1 to 200, wherein the group Y is selected from the group consisting of (a) an aliphatic or cycloaliphatic oligoamine selected from the group consisting of diethylenetriamine, dipropylenetriamine, triethylenetetramine, tetraethylenepentamine, pentaethylenehexamine, N(2-aminoethyl)-1,3-propanediamine, N,N-dimethylethanolamine, diethanolamine, triethanolamine, 3-dimethylamino-1-propanol, N-(2-aminoethyl) ethanol amine, 3-(dimethylamino) propylamine, N,N'-bis(3-aminopropyl)-1,2-ethylenediamine, N,N,N',N'-tetrakis(3-aminopropyl)-1,2-ethylenediamine, N,N,N',N'-tetrakis[3-($C_1$- to $C_4$-alkylamino)propyl]-1,2-ethylenediamine, N,N'-bis (3-aminopropyl)piperazine and N,N'-bis[3-($C_1$- to $C_4$-alkylamino)propyl]piperazine;

(b) a polyethyleneimine of the formula (III)

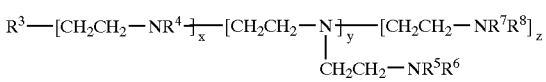

(III)

which has an average molecular weight ($M_W$) ranging from 200 to 1,000,000 and wherein radicals $R^3$ to $R^8$ are independently hydrogen, linear or branched $C_1$- to $C_{20}$-alkyl, -alkoxy, -polyoxyethylene, -hydroxyalkyl, -(alkyl)carboxy, -phosphonoalkyl, -alkylamino radicals, $C_2$- to $C_{20}$-alkenyl radicals or $C_6$- to $C_{20}$-aryl, -aryloxy, -hydroxyaryl, -arylcarboxy or -arylamino radicals which optionally are substituted, and $R^4$ and $R^5$ are each additionally polyethyleneimine polymer chains, and x, y and z are independently 0 or an integer, (c) a polyamidoamine which has an average molecular weight ($M_W$) ranging from 500 to 100,000,000, which is prepared by reaction of $C_4$- to $C_{10}$-dicarboxylic acids with poly($C_2$- to $C_4$-alkylene)polyamines having from 3 to 20 basic nitrogen atoms in the molecule and which has at least m' primary and/or secondary amino groups which form amide bonds with the structural unit (I);

(d) a polyamine of formula (IV)

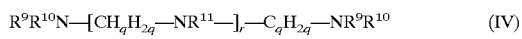

(IV)

which has an average molecular weight ($M_W$) ranging from 100 to 100,000,000 and wherein the radicals $R^9$ to $R^{11}$ are independently hydrogen, linear or branched $C_1$- to $C_{20}$-alkyl, -alkoxy, -polyoxyethylene, -hydroxyalkyl, -(alkyl)carboxy, -phosphonoalkyl, -alkylamino radicals, $C_2$- to $C_{20}$-alkenyl radicals or $C_6$- to $C_{20}$-aryl, -aryloxy, -hydroxyaryl, -arylcarboxy or -arylamino radicals which optionally are substituted, q is an integer from 2 to 6 and r is an integer, wherein the alkylamino radicals mentioned are optionally continued in the alkyl moiety; and (e) a polyvinylamine of formula (V)

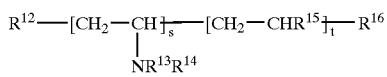

which has an average molecular weight ($M_W$) ranging from 300 to 100,000,000 and wherein $R^{12}$ to $R^{16}$ are independently hydrogen, linear or branched $C_1$- to $C_{20}$alkyl, -alkoxy, -polyoxyethylene, -hydroxyalkyl, -(alkyl)carboxy, -phosphonoalkyl, -alkylamino radicals, $C_2$- to $C_{20}$-alkenyl radicals or $C_6$- to $C_{20}$-aryl, -aryloxy, -hydroxyaryl, -arylcarboxy or -arylamino radicals which optionally are substituted, and $R^{15}$ is additionally a formamidyl radical, s is an integer and t is 0 or an integer.

2. The method as claimed in claim 1, wherein said textile fibers contain at least one compound (A) containing at least one structural unit (I) to protect dyed textile material against fading.

3. The method as claimed in claim 1, wherein compound (A) conforms to formula (II) and wherein the number m of the structural units (I) in the compounds (II) is 1, 2 or 3.

4. The method as claimed in claim 1, wherein compound (A) contains at least one structural unit (I) where X is a group of the formula —$CR^1$=$CR^2$— where $R^1$ and $R^2$ are independently hydrogen, cyano or unsubstituted phenyl or where $R^1$ is the group —NH—CO—, which is bonded with its carbonyl carbon atom to the ortho position of the adjacent phenyl ring to form a benzopyrrolidone system, and $R^2$ is also cyano, and n is 1.

5. The method as claimed in claim 1, wherein compound (A) contains at least one structural unit (I) where Z is a substituent selected from the group consisting of $C_1$- to $C_8$-alkoxy, amino, mono- or di-$C_1$- to $C_8$-alkylamino and hydroxyl and p is 1.

6. The method as claimed in claim 1, wherein compound (A) contains at least one structural unit (I) as UV absorbers for cellulosic textile material which possesses affinity for textile fiber.

7. A method of treating textile fibers, comprising:

imparting UV light protection properties to textile fibers by treating the textile fibers with a compound having UV light absorption properties that contains at least one structural unit of formula (II)

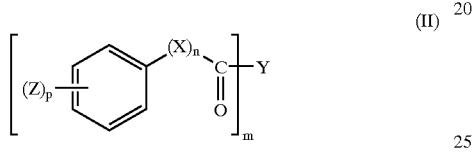

and that adheres to the textile fibers, wherein

X is a group of the formula —$CR^1$=$CR^2$—, where $R^1$ and $R^2$ are independently hydrogen, $C_1$- to $C_8$-alkyl, $C_1$- to $C_8$-alkoxy, $C_1$- to $C_8$-alkoxycarbonyl, $C_1$- to $C_8$-acyloxy, carboxyl, cyano, nitro, fluorine, chlorine, bromine, sulfonyl, $C_1$- to $C_8$-alkylsulfonyl or phenyl which may be substituted by up to 3 radicals selected from the group consisting of $C_1$- to $C_8$-alkyl, $C_1$- to $C_8$-alkoxy, $C_1$- to $C_8$-alkoxycarbonyl, $C_1$- to $C_8$-acyloxy, carboxyl, cyano, nitro, chlorine, bromine, sulfonyl and $C_1$- to $C_8$-alkylsulfonyl, where $R^1$ optionally is the group —NQ—CO—, which is bonded with its carbonyl carbon atom to the ortho position of the adjacent phenyl ring to form a benzopyrrolidone system, and in which Q is hydrogen or a $C_1$–$C_8$-alkyl radical;

Z is a substituent selected from the group consisting of $C_1$- to $C_8$-alkyl, $C_1$- to $C_8$ alkoxy, $C_1$- to $C_8$-alkoxycarbonyl, $C_1$- to $C_8$-acyloxy, carboxyl, cyano, nitro, fluorine, chlorine, bromine, sulfonyl, $C_1$- to $C_8$-alkylsulfonyl, amino, mono- or di-$C_1$- to $C_8$-alkylamino, carboxamido (with or without one or two $C_1$- to $C_8$-alkyl groups on the amide nitrogen), hydroxyl and saturated or unsaturated five- and six-membered heterocyclic radicals, which may be benzofused, and any two adjacent Z substituents may also form a saturated or unsaturated five- or six-membered ring, and in the case of p=0 an ortho-disposed carboxyl group may be combined with the carbonyl group present and a nitrogen atom attached directly to this cyclic group to form a cyclic imide;

n is 1, 2 or 3 and p is 0, 1, 2, 3, 4 or 5;

Y is the radical of an aliphatic, cycloaliphatic, or mixed aliphatic-aromatic group which has at least me primary and/or secondary amino groups, which are capable of forming amide bonds with the structural unit of the formula (I)

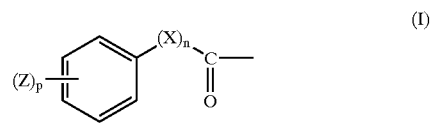

and the tertiary and/or free primary and/or secondary nitrogen atoms present in the compounds of radical Y optionally being quaternized; and m is the number of structural units (I) bonded to primary and/or secondary amino groups and hydroxyl groups and accounts for from 10 to 100% of the number of these m' groups which range from 1 to 200, wherein Y is the radical of a compound selected from the group consisting of;

(a) an aliphatic or cycloaliphatic oligoamine selected from the group consisting of diethylenetriamine, dipropylenetriamine, triethylenetetramine, tetraethylenepentamine, pentaethylenehexamine, N-2-aminoethyl)-1,3-propanediamine, 3-(dimethylamino) propylamine, N,N'-bis(3-aminopropyl)-1,2-ethylenediamine, N,N,N',N'-tetrakis(3-aminopropyl)-1,2-ethylenediamine, N,N,N',N'-tetrakis[3-($C_1$- to $C_4$-alkylamino)propyl]-1,2-ethylenediamine, N,N'-bis (3-aminopropyl)piperazine and N,N'-bis[3-($C_1$- to $C_4$-alkylamino)propyl]piperazine;

(b) a polyethyleneimine of the formula (III)

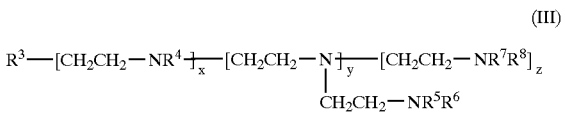

which has an average molecular weight ($M_W$) ranging from 200 to 1,000,000 and wherein radicals $R^3$ to $R^8$ are independently hydrogen, linear or branched $C_2$- to $C_{20}$-alkyl, -alkoxy, (alkyl)carboxy, -phosphonoalkyl, -alkylamino radicals, $C_2$- to $C_{20}$-alkenyl radicals or $C_6$- to $C_{20}$-aryl, -aryloxy, -arylcarboxy or -arylamino radicals which optionally are substituted, and $R^4$ and $R^5$ are each additionally polyethyleneimine polymer chains, and x, y and z are independently 0 or an integer;

(c) a polyamidoamine which has an average molecular weight ($M_W$) ranging from 500 to 100,000,000, which is prepared by reaction of $C_4$- to $C_{10}$-dicarboxylic acids with poly($C_2$- to $C_4$-alkylene)polyamines having from 3 to 20 basic nitrogen atoms in the molecule and which has at least m' primary and/or secondary amino groups which form amide bonds with the structural unit (I);

(d) a polyamine of formula (IV)

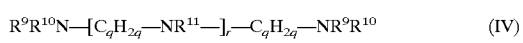

which has an average molecular weight ($M_W$) ranging from 100 to 100,000,000 and wherein the radicals $R^9$ to $R^{11}$ are independently hydrogen, linear or branched $C_1$- to $C_{20}$-alkyl, -alkoxy, -(alkyl)carboxy, -phosphonoalkyl, -alkylamino radicals, $C_2$- to $C_{20}$-alkenyl radicals or $C_6$- to $C_{20}$-aryl, -aryloxy, -arylcarboxy or -arylamino radicals which optionally are substituted, q is an integer from 2 to 6 and r is an integer, wherein the alkylamino radicals mentioned are optionally continued in the alkyl moiety; and (e) a polyvinylamine of formula (V)

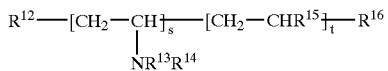

which has an average molecular weight ($M_w$) ranging from 300 to 100,000,000 and wherein $R^{12}$ to $R^{16}$ are independently hydrogen, linear or branched $C_1$- to $C_{20}$-alkyl, -alkoxy, -(alkyl)carboxy, -phosphonoalkyl, -alkylamino radicals, $C_2$- to $C_{20}$-alkenyl radicals or $C_6$- to $C_{20}$-aryl, -aryloxy, -arylcarboxy or -arylamino radicals which optionally are substituted, and $R^{15}$ is additionally a formamidyl radical, s is an integer and t is 0 or an integer.

8. The method as claimed in claim 1, wherein compound (A) is applied to the textile fibers by laundering fabric and by laundry pre- or after-treatment.

* * * * *